US009222895B2

(12) United States Patent
Duffy et al.

(10) Patent No.: US 9,222,895 B2
(45) Date of Patent: Dec. 29, 2015

(54) GENERALIZED VIRTUAL INSPECTOR (71) Applicant: KLA-Tencor Corporation, Milpitas, CA (US)

(72) Inventors: Brian Duffy, San Jose, CA (US); Kris Bhaskar, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 4 days.

(21) Appl. No.: 14/184,417

(22) Filed: Feb. 19, 2014

(65) Prior Publication Data

US 2014/0241610 A1  Aug. 28, 2014

Related U.S. Application Data (60) Provisional application No. 61/768,879, filed on Feb. 25, 2013, provisional application No. 61/807,643, filed on Apr. 2, 2013, provisional application No. 61/812,328, filed on Apr. 16, 2013.

(51) Int. Cl.
G06F 17/50 (2006.01)
G01N 21/95 (2006.01)
G06T 7/00 (2006.01)
G06T 7/60 (2006.01)

(52) U.S. Cl.
CPC .......... *G01N 21/9501* (2013.01); *G06T 7/0051* (2013.01); *G06T 7/602* (2013.01); *G06T 2207/10016* (2013.01); *G06T 2207/30252* (2013.01)

(58) Field of Classification Search
USPC .......................................................... 716/136
See application file for complete search history.

(56) References Cited

U.S. PATENT DOCUMENTS

| 5,321,505 | A  | 6/1994  | Leddy |
| 5,761,064 | A  | 6/1998  | La et al. |
| 6,377,898 | B1 | 4/2002  | Steffan et al. |
| 6,645,780 | B1 | 11/2003 | Sonderman et al. |
| 6,759,655 | B2 | 7/2004  | Nara et al. |
| 6,855,568 | B2 | 2/2005  | Weiner et al. |
| 6,876,445 | B2 | 4/2005  | Shibuya et al. |
| 6,886,153 | B1 | 4/2005  | Bevis |
| 6,898,304 | B2 | 5/2005  | Naftali et al. |
| 6,952,656 | B1 | 10/2005 | Cordova et al. |
| 6,985,220 | B1 | 1/2006  | Chen et al. |
| 6,990,385 | B1 | 1/2006  | Smith et al. |

(Continued)

FOREIGN PATENT DOCUMENTS

WO   2012/033484   3/2012

OTHER PUBLICATIONS

International Search Report and Written Opinion for PCT/US2014/017792 mailed Jun. 17, 2014.

*Primary Examiner* — Paul Dinh
*Assistant Examiner* — Bryce Aisaka
(74) *Attorney, Agent, or Firm* — Ann Marie Mewherter (57) ABSTRACT Generalized virtual inspectors are provided. One system includes two or more actual systems configured to perform one or more processes on specimen(s) while the specimen(s) are disposed within the actual systems. The system also includes one or more virtual systems coupled to the actual systems to thereby receive output generated by the actual systems and to send information to the actual systems. The virtual system(s) are configured to perform one or more functions using at least some of the output received from the actual systems. The virtual system(s) are not capable of having the specimen(s) disposed therein.

43 Claims, 3 Drawing Sheets (56) References Cited

U.S. PATENT DOCUMENTS

| | | | |
|---|---|---|---|
| 7,024,339 | B1 | 4/2006 | Bhaskar et al. |
| 7,184,152 | B2 | 2/2007 | Brill |
| 7,251,586 | B2 | 7/2007 | Bhaskar et al. |
| 7,379,847 | B1 | 5/2008 | Blecher et al. |
| 7,437,510 | B2 | 10/2008 | Rosenbluth et al. |
| 7,440,640 | B1 | 10/2008 | Bhaskar et al. |
| 7,440,942 | B2 | 10/2008 | Dixon et al. |
| 7,522,664 | B1 | 4/2009 | Bhaskar et al. |
| 7,570,796 | B2 | 8/2009 | Zafar et al. |
| 7,676,077 | B2 | 3/2010 | Kulkarni et al. |
| 7,796,804 | B2 | 9/2010 | Bhaskar et al. |
| 7,877,722 | B2 | 1/2011 | Duffy et al. |
| 7,904,845 | B2 | 3/2011 | Fouquet et al. |
| 8,041,103 | B2 | 10/2011 | Kulkarni et al. |
| 8,126,255 | B2 | 2/2012 | Bhaskar et al. |
| 8,139,843 | B2 | 3/2012 | Zafar et al. |
| 8,194,968 | B2 | 6/2012 | Park et al. |
| 8,223,327 | B2 | 7/2012 | Chen et al. |
| 8,559,001 | B2 | 10/2013 | Chang et al. |
| 8,611,639 | B2 | 12/2013 | Kulkarni et al. |
| 2001/0053557 | A1 | 12/2001 | Park |
| 2002/0072133 | A1 | 6/2002 | Jun et al. |
| 2002/0167487 | A1* | 11/2002 | Miller .................. G06T 7/001 345/156 |
| 2005/0094136 | A1 | 5/2005 | Xu et al. |
| 2006/0030060 | A1 | 2/2006 | Noguchi et al. |
| 2006/0209313 | A1 | 9/2006 | Van Den Akker et al. |
| 2007/0156379 | A1 | 7/2007 | Kulkarni et al. |
| 2007/0159179 | A1 | 7/2007 | Park et al. |
| 2007/0288219 | A1 | 12/2007 | Zafar et al. |
| 2008/0013083 | A1 | 1/2008 | Kirk et al. |
| 2008/0018887 | A1 | 1/2008 | Chen et al. |
| 2008/0032429 | A1 | 2/2008 | Chen et al. |
| 2008/0068036 | A1 | 3/2008 | Yun et al. |
| 2008/0148216 | A1* | 6/2008 | Chan et al. ............... 716/19 |
| 2008/0163140 | A1 | 7/2008 | Fouquet et al. |
| 2008/0250384 | A1 | 10/2008 | Duffy et al. |
| 2009/0080759 | A1 | 3/2009 | Bhaskar et al. |
| 2009/0307163 | A1 | 12/2009 | Jang et al. |
| 2011/0304527 | A1 | 12/2011 | Wu et al. |
| 2012/0093392 | A1* | 4/2012 | Takagi et al. .................. 382/149 |
| 2013/0103336 | A1 | 4/2013 | Amini et al. |
| 2013/0208973 | A1 | 8/2013 | Brill |
| 2013/0267047 | A1* | 10/2013 | Shih et al. ................. 438/14 |

* cited by examiner

GENERALIZED VIRTUAL INSPECTOR

BACKGROUND OF THE INVENTION

1. Field of the Invention

The present invention generally relates to generalized virtual inspectors.

2. Description of the Related Art

The following description and examples are not admitted to be prior art by virtue of their inclusion in this section.

Automated surface inspection is important to a number of different fields. For instance, inspection is substantially important when fabricating semiconductors to improve yields and provide process control. Surface inspection is particularly challenging for semiconductor wafers in that the dimensions of structures present on the surface are extremely small and are continuously getting smaller as technology progresses. The size of the structures requires inspection systems to have extremely high resolution, which in turn translates to a substantially large amount of data collected during the inspection process. For example, the inspection of a single 300 mm diameter wafer may generate in excess of 15 terapixels of image data collected in less than 60 minutes when using current inspection systems such as the 29xx system, which is commercially available from KLA-Tencor, Milpitas, Calif.

Because of the enormous amount of data generated by inspection, common practice is to design wafer inspection systems so that they process the acquired data rapidly since storing this amount of data would be either substantially expensive or practically impossible due to the underlying limitations of the technology used in the computers implementing the inspection algorithms. For example, current wafer inspection systems may utilize multiple processors (called nodes) with dedicated memory in each to distribute the computation toad required to handle data streaming in from a sensor. This data may be partitioned into swaths across the wafer, and the swaths may be further sub-divided into sub-swaths, each sub-swath being processed by one node. The results of computation are passed to a host computer, and the memory of each node is cleared to make way for the data for the next (sub) swath. No "state" information about the previous scan is retained. In other words, the data from the sensor is discarded when the node reaches the end of the swath. As such, the node has no memory across scans.

Therefore, due to the large amount of data acquired, most wafer inspection has been implemented by providing image processing equipment capable of executing a defect detection algorithm at speeds matching those of the data acquisition apparatus. Executing the defect detection algorithm at such speeds often limits the complexity of the algorithm used. In particular, relatively simple algorithms may be used to ensure that the data is processed as fast as it is acquired. Alternatively, more complex defect detection algorithms that process data slower than the data acquisition rate may be used, but such algorithms require slower data acquisition thereby reducing the overall throughput of the inspection system.

Accordingly, it would be advantageous to develop systems and methods for creating persistent data for a wafer and using persistent data for inspection-related functions.

SUMMARY OF THE INVENTION

The following description of various embodiments is not to be construed in any way as limiting the subject matter of the appended claims.

One embodiment relates to a system configured to perform one or more actual processes and one or more virtual processes for a specimen. The system includes two or more actual systems configured to perform one or more processes on one or more specimens white the one or more specimens are disposed within the two or more actual systems. The one or more specimens include a wafer. The system also includes one or more virtual systems coupled to the two or more actual systems to thereby receive output generated by the two or more actual systems and to send information to the two or more actual systems. The one or more virtual systems are configured to perform one or more functions using at least some of the output received from the two or more actual systems. The one or more virtual systems are not capable of having the one or more specimens disposed therein. Each of the embodiments of the system described above may be further configured as described further herein.

An additional embodiment relates to a method for performing one or more actual processes and one or more virtual processes for a specimen. The method includes performing one or more processes on one or more specimens with two or more actual systems while the one or more specimens are disposed within the two or more actual systems. The one or more specimens include a wafer. The method also includes receiving output generated by the two or more actual systems with one or more virtual systems coupled to the two or more actual systems. In addition, the method includes sending information from the one or more virtual systems to at least one of the two or more actual systems. The method further includes performing one or more functions with the one or more virtual systems using at least some of the output received from the two or more actual systems. The one or more virtual systems are not capable of having the one or more specimens disposed therein.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for performing one or more actual processes and one or more virtual processes for a specimen. The computer-implemented method includes receiving output generated by two or more actual systems with one or more virtual systems coupled to the two or more actual systems. The two or more actual systems perform one or more processes on one or more specimens while the one or more specimens are disposed within the two or more actual systems. The one or more specimens include a wafer. The computer-implemented method also includes sending information from the one or more virtual systems to at least one of the two or more actual systems. In addition, the computer-implemented method includes performing One or more functions with the one or more virtual systems using at least some of the output received from the two or more actual systems. The one or more virtual systems are not capable of having the one or more specimens disposed therein.

The computer-readable medium may be further configured as described herein. The steps of the computer-implemented method may be performed as described further herein. In addition, the computer-implemented method for which the program instructions are executable may include any other step(s) of any other methods(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

In general, the embodiments described herein are configured to perform one or more actual processes and one or more virtual processes for one or more specimens that include a wafer. The embodiments described herein integrate and extend the efficiencies of offline image data analysis for high cost (or time intensive) image acquisition sources combined with inspection, metrology, and test applications (e.g., electrical, image-based, or any other test applications), which can benefit from multiple live, recorded, simulated, or "fused" image data sources. The embodiments enable a deployable, user-accessible, and field-adaptable elegant ecosystem of applications and data. The embodiments also maximize tool availability for production. In addition, the embodiments can reduce queuing interdependencies (e.g., between personnel, tools, wafers, etc.). The embodiments can also minimize learning loops that normally require returning to tools (by allowing all relevant data to be acquired once and stored in its entirety). Furthermore, the embodiments described herein can minimize result variability due to human judgment and/or error. Moreover, the embodiments described herein enable new applications that were previously not practical for reasons including those mentioned above.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. The embodiments described herein can be used for wafers that have incompletely fabricated devices formed thereon or completely fabricated devices formed thereon. For example, the specimen may include a wafer or sub-wafer or packaging thereof at any physically observable stage in its process flow. Many different types of devices such as integrated circuits (ICs) may be formed on a wafer, and the term wafer as used herein is intended to encompass a wafer on which any type of device known in the art is being fabricated.

The one or more specimens may also include a reticle, which may also be commonly referred to as a mask or a photomask. Many different types of reticles are known in the art, and the terms "reticle," "mask," and "photomask" as used herein are intended to encompass all types of reticles known in the art. The specimen(s) may also include one or more reticles for one or more of the patterning layers of the wafer or package of interest.

The term "design data" as used herein generally refers to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design data. Such a reticle image or a derivative thereof can serve as a substitute for the design layout in any embodiments described herein that use design data. The design data may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to perform one or more actual processes and one or more virtual processes for a specimen. In general, "actual processes" as that term is used herein refer to processes that are performed on or using an actual, physical specimen. In contrast, a "virtual process" as that term is used herein refers to a process that may be performed for a specimen without using or interacting with the actual, physical specimen.

The system includes two or more actual systems configured to perform one or more processes on one or more specimens while the one or more specimens are disposed within the two or more actual systems. In general, the one or more processes performed on the specimen(s) by the actual systems are yield control-related processes such as inspection, review, metrology, testing, and the like. The processes performed by the actual systems are not meant to include processes that are performed by reticle or wafer fabrication tools that alter one or more characteristics of the reticle or wafer. For example, a wafer removed from a wafer inspection tool will have substantially the same characteristics as it did when it was placed inside the wafer inspection tool (unless, of course, something goes terribly wrong) However, there may be some instances in which a yield-control related process may alter one or more characteristics of the specimen, but those characteristics that are altered are not meant to alter the function of devices being formed on or with the specimen. For example, intentional "burn marks" may be left by a SEM to aid in subsequent relocation of a specific point. Note that for some surfaces it is common for charging from the SEM to unintentionally leave a "burn mark." Such charging or burning can be advantageously avoided using the embodiments described herein since the recorded image of the wafer can be used for re-inspection even when the state of the physical wafer has been changed by the SEM. In contrast, a wafer removed from a fabrication tool will typically have different characteristics (physical, chemical, and the like) as it did when it was placed inside the fabrication tool (again, unless something goes wrong such as process fail) that will alter the characteristic(s) of devices being formed on or with the specimen.

Since the two or more actual systems perform the process(es) on the specimen(s) while the specimens are disposed within the actual systems, the actual systems will include some sort of specimen handling device or subsystem (such as a stage, a motor driving the stage, a wafer or reticle handling robot, etc.). The specimen handling device or subsystem will generally control the position of the specimen within the actual system. In this manner, the actual systems described herein are configured to perform process(es) on the physical specimen itself, which is in contrast to the virtual systems described further herein that do not interact with the physical specimens even though they can perform one or more functions for the physical specimens.

Performing the process(es) on the specimen(s) with the actual systems will generally cause some output (e.g., images, data, image data, signals, image signals, etc.) to be generated by the actual systems. For example, during a process, a detector or sensor of an actual system may generate one or more images of a specimen. In this manner, the actual systems may, in the context of the description contained herein, be source tools in that they provide image sources. The actual systems may also include one or more computer subsystems that perform some function, algorithm, or method on the output generated by the one or more detectors or sensors of the actual systems. For example, a computer subsystem of an actual system may perform defect detection for a specimen using output generated by a detector of the actual system. The results of that defect detection or any other function, method, or algorithm may also be output from the actual systems as described further herein. Therefore, the actual systems described herein may produce a variety of output, all or only some of which may be received by one or more virtual systems as described further herein.

Figure 1:
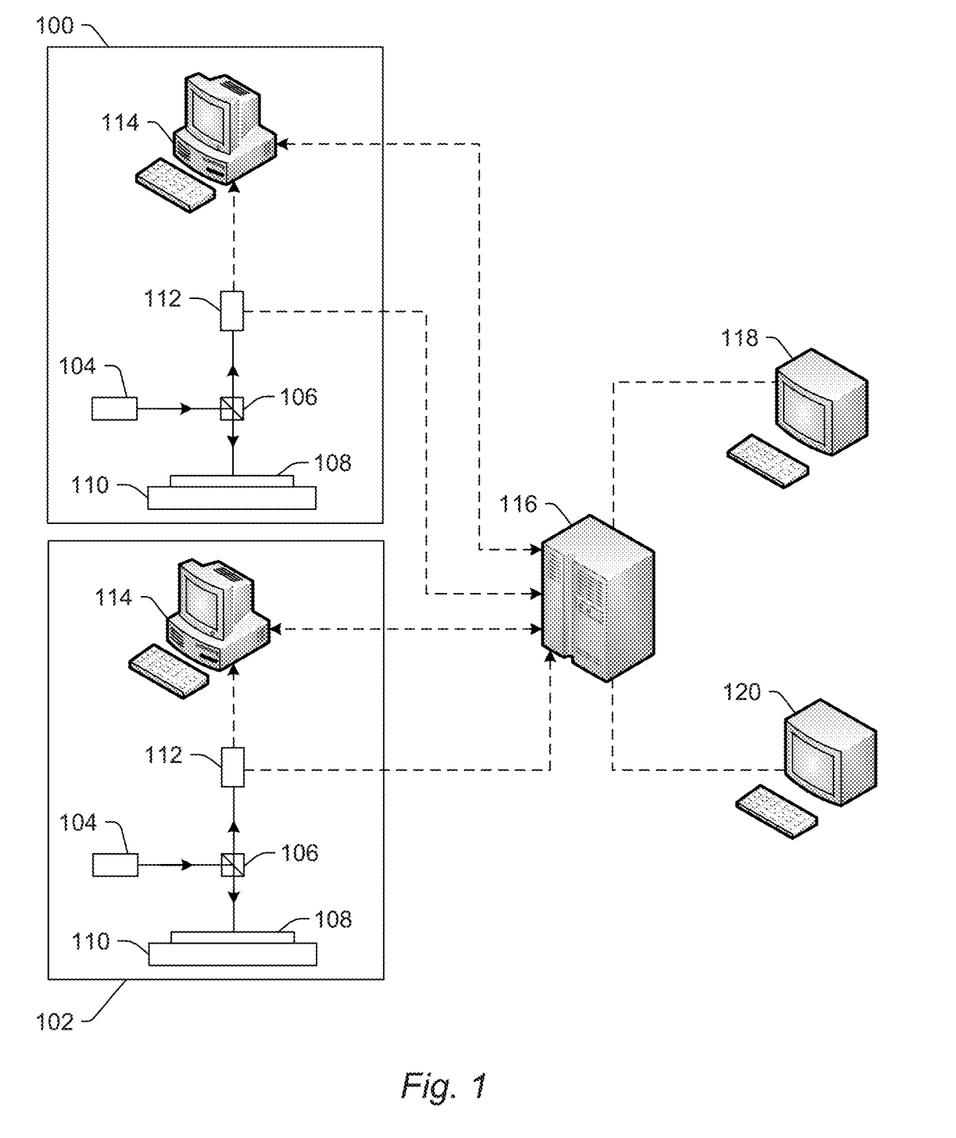
FIG. 1 is a schematic diagram illustrating a side view of one embodiment of a system configured to perform one or more actual processes and one or more virtual processes for a specimen.

In one embodiment, the two or more actual systems include two of the same systems. For example, as shown in FIG. 1, the system may include two actual systems 100 and 102. In this embodiment, each of the two actual systems includes light source 104 configured to generate light. The actual systems also include beam splitter 106 that is configured to direct light from the light source to specimen 108. Specimen 108 is supported within each of the actual systems by stage 110. Light reflected, scattered, diffracted, or otherwise returned from the specimen may be transmitted by beam splitter 106 to detector 112, which is included in each of the actual systems. The detectors are configured to generate output such as images, image data, signals, or any other suitable output responsive to the light detected by the detectors.

The output of the detectors may be received by computer subsystems 114 included in each of the actual systems. Computer subsystems 114 may be coupled to each of the detectors in any suitable manner. The computer subsystems may be configured to determine one or more characteristics of the specimen using the output of the detectors. The one or more characteristics that are determined by the computer subsystems will vary depending on the configuration of the actual system and specimen on which an actual process is being performed.

The two or more actual systems shown in FIG. 1, therefore, have the same configuration and therefore may be the same type of system. However, at any given point in time, the setup of the actual systems may be different. For example, if one of the actual systems is being used to inspect one type of wafer while another of the actual systems is being used to inspect a different type of wafer, a value of a parameter of the one actual system may be different than a value of the parameter of the other actual system. For example, if the light sources included in the actual systems have multiple wavelengths, one or more of the wavelengths may be used to inspect one type of wafer and other wavelength(s) may be used to inspect another type of wafer.

In another embodiment, the two or more actual systems include two systems having different configurations. For example, any of the elements shown in FIG. 1 of one or more of the actual systems may be selected to be different. In one such example, the actual systems may have different types of light sources, may be configured to perform one or more processes on different specimens, may have different detectors, etc. In general, the actual systems included in the system embodiments described herein may include any type of actual systems in any numbers and combinations.

It is noted that FIG. 1 is provided herein to generally illustrate one configuration of the actual systems that may be included in the system embodiments described herein. Obviously, the actual system configurations described herein may be altered to optimize the performance of the actual systems as is normally performed when designing a wafer or reticle-based yield control-related system. In addition, the systems described herein may be implemented using existing actual systems (e.g., by adding functionality described herein to existing actual systems) such as the tools that are commercially available from KLA-Tencor, Milpitas, Calif. Alternatively, the system described herein may be designed "from scratch" to provide a completely new system.

In some embodiments, the two or more actual systems are configured to perform the process(es) on more than one of the specimen(s) simultaneously. For example, the actual systems included in the system may each be configured as physically separated systems, which may be coupled by other hardware or software as described further herein. Therefore, the actual systems may be used to perform processes on specimens at the same time (although not the same specimen at the same time).

In another embodiment, the two or more actual systems are configured to perform the process(es) on the specimen(s) independently of each other. For example, since the actual systems included in the system may be each configured as physically separated systems, the actual systems may perform their processes independently of any of the other actual systems. Control of the actual systems may be performed as described further herein. In addition, as described further herein, in some instances, it may be advantageous to perform one or more processes with one actual system based on results of one or more processes of another system. Therefore, in some instances, there may be interdependencies in the processes performed by the actual systems.

Figure 2:
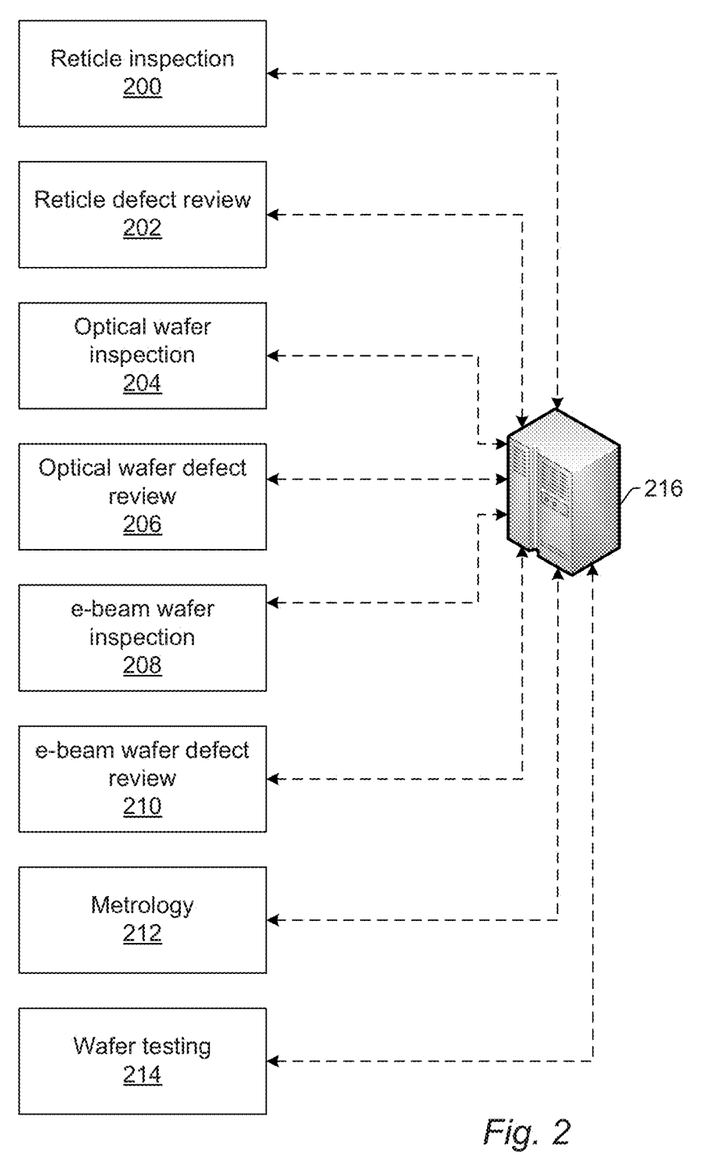
FIGS. 2-3 are block diagrams illustrating embodiments of a system configured to perform one or more actual processes and one or more virtual processes for a specimen.

In one embodiment, the two or more actual systems include at least one reticle inspection system or reticle defect review system. For example, as shown in FIG. 2, the system may include reticle inspection system 200 and/or reticle defect review system 202. The reticle inspection or defect review system may be an optical-based system or an electron beam-based system. In addition, the actual systems may include both reticle inspection and defect review systems. Furthermore, the same actual system may be configured for both reticle inspection and defect review. The reticle inspection and/or defect review system may include any suitable commercially available systems. In addition, the reticle inspection and/or defect review systems may be configured to perform any kind of inspection and/or review. The reticle inspection and/or defect review systems may also be configured to acquire output for the reticle by scanning the reticle or in a step and repeat fashion (also sometimes referred to as move-acquire-measure). Output generated by the reticle inspection and/or defect review system may also include reticle area images or reticle point images. In addition, the reticle inspection and/or defect review systems may be configured to acquire images or data for the reticle in multiple imaging modes.

In some embodiments, the two or more actual systems include at least one wafer inspection system or wafer defect review system, and the at least one wafer inspection system or wafer defect review system is a light-based system. For example, as shown in FIG. 2, the system may include optical wafer inspection system 204 and/or optical wafer defect review system 206. In this manner, the actual systems may include one or more of a wafer inspection system, a wafer defect review system, or a wafer inspection and defect review system. The light-based wafer inspection and/or defect review system may include any suitable commercially available systems such as the Puma systems, the 2915 systems, and the SPx, Surfscan, and Surfimage systems that are commercially available from KLA-Tencor. In addition, the light-based wafer inspection and/or defect review systems may be configured to perform any kind of inspection and/or review such as dark field (DF) laser scattering, narrow band bright field (BF), broadband BF, etc. The light-based wafer inspection and/or defect review systems may also include any suitable light source such as a broadband plasma-based light source. The wafer inspection and/or defect review systems may also be configured to acquire output for the wafer by scanning light over the wafer or in a step and repeat fashion (also sometimes referred to as move-acquire-measure). Output generated by the wafer inspection and/or defect review system may also include wafer area images or wafer point images. In addition, the wafer inspection and/or defect review systems may be configured to acquire images or data for the wafer in multiple imaging modes.

In another embodiment, the two or more actual systems include at least one wafer inspection system or wafer defect review system, and the at least one wafer inspection system or wafer defect review system is an electron beam-based system. For example, as shown in FIG. 2, the system may include e-beam wafer inspection system 208 and/or e-beam wafer defect review system 210. In this manner, the actual systems may include one or more of a wafer inspection system, a wafer defect review system, or a wafer inspection and defect review system. The electron beam-based wafer inspection and/or defect review system may be configured to generate wafer point or area images. The electron beam-based wafer inspection and/or defect review system may include any suitable commercially available systems such as the es805 and EDR7100 systems that are commercially available from KLA-Tencor.

In some embodiments, the one or more actual systems include at least one metrology system. For example, as shown in FIG. 2, the system may include metrology system 212. The metrology system may include any suitable commercially available metrology system. The metrology system may be configured to measure or determine any one or more characteristics of any of the specimens described herein. For example, the metrology system may be configured as a scatterometry system that is configured to measure or determine a critical dimension or critical dimension uniformity of patterned features on a wafer. Metrology systems are generally different than inspection systems in that the metrology systems do not scan over wafers or reticles generating output at each location that is scanned. Instead, metrology systems often perform measurements at one or a limited number of measurements spots on a wafer or reticle in a move-acquire-measure type scenario. In some instances, the metrology system may perform measurements based on output or results of another actual system described herein. For example, the metrology system may be used to measure one or more characteristics of defects detected by inspection. Control of the metrology system in this manner may be further performed as described herein.

In a further embodiment, the one or more actual systems include at least one wafer testing system, and the wafer testing system includes an electrical testing-based system. For example, as shown in FIG. 2, the system may include wafer testing system 214. The wafer testing system may include any suitable commercially available wafer testing system. The electrical testing-based system may be a contact type system in which one or more elements of the system make contact with one or more device structures formed on the wafer in order to establish an electrical connection between the wafer and the tester. Alternatively, the electrical testing-based system may be a non-contact type system in which none of the elements makes contact with the wafer during the testing.

Although a variety of specific actual systems are described herein, it is to be understood that the invention is not limited to these specific actual systems. For example, it is conceivable that any actual system configured to perform one or more processes on a wafer and/or reticle may be included in the system and coupled to the virtual system(s) as described herein. In one such example, the actual systems may also include failure analysis tools and/or materials analysis tools. In addition, the actual systems may be a combination of tools that are available from different suppliers as long as the tools meet certain interface standards (e.g., the ability to interface with the virtual systems described further herein).

The system also includes one or more virtual systems coupled to the two or more actual systems to thereby receive output generated by the two or more actual systems and to send information to the two or more actual systems. For example, as shown in FIG. 1, actual systems 100 and 102 are coupled to virtual system 116. In one embodiment, detectors 112 of the actual systems may be coupled to the virtual system so that output of the detectors may be sent directly to the virtual system. In this manner, the virtual system may receive raw output of the detectors (i.e., output upon which no data, signal, or other processing has been performed). In addition or alternatively, computer subsystems 114 of the actual systems may be coupled to the virtual system so that the computer subsystems can send output of the detectors and/or any other information generated by the computer subsystems to the virtual system. The virtual system may also be coupled to both a computer subsystem and a detector of an actual system. The virtual system may be coupled to any components of the actual systems as described further herein.

As described above, the actual systems may include a variety of different actual systems in any combination. Therefore, the output received from the two or more actual systems may be different and vary depending on the configuration of the actual system and/or the actual process(es) performed on the specimen(s) by the actual systems. For example, the output may include mapping of spatially continuous data (such as may be generated by a scanning actual system), spatially discrete data (such as may be generated by a move-acquire-measure system), metrology data, point defect detection data, etc.

The configuration of the virtual system(s) and the number of virtual systems included in the system may vary greatly. In addition, the configuration and number of virtual systems included in the system may be changed at any point in time. For example, the system may be configured to mix and match virtual systems for reliability, hot swapping, capacity expansion, data mining, cross-correlation, and any other functions described herein.

The virtual systems may be coupled to the actual systems in any suitable manner. For example, the virtual systems may be coupled to the actual systems via interfaces to enable controlled transfer of actual system output and various information between the actual systems and the virtual systems. The virtual and actual systems my also or alternatively be coupled to each other for output and information transfer through an intermediate abstracted "machine control" layer. Any of the virtual systems and actual systems that exist simultaneously can be coupled to each other. Furthermore, the virtual and actual systems may interact with each other according to standard factory automation protocols. In addition, the virtual systems may be coupled to post-processing data analysis systems in a similar manner. The post-processing data analysis systems may include computer subsystem(s) of the actual systems or other computer-based systems that may or may not include specimen handling capabilities.

The systems described herein, therefore, provide relatively tight coupling between source-specific implementations to achieve multi-source benefits. In addition, the systems provide flexible, multiplexed, general purpose configurations that accommodate multiple sources. The systems may also be configured for farming generalized virtual systems to achieve desired reliability and capacity. The virtual and actual systems also may or may not be located in physical proximity to one another. In addition, the virtual systems may be configured as a virtual "mega-tool" via high speed links between various actual and virtual systems. In another example, the systems described herein may be implemented as a single generalized virtual system realized by connecting multiple actual units via substantially high bandwidth connections in a manner similar to in multi-column image computers on inspectors. A system that includes multiple virtual systems may integrate those systems with centralized or distributed packaging, leveraging substantially high speed networking. In another embodiment, multiple virtual system-like software packages may be linked via a relatively high speed network, and the system can include only one virtual system. In addition, the system may include at least one super high bandwidth link for scanning optical inspectors and at least one substantially high capacity link for electron beam-based tools. Data received via these links can be stored and processed simultaneously from different specimens. Furthermore, the systems described herein may be configured as a tightly coupled recipe management and distribution system as described further herein. The systems also provide an efficient, data (meta-data) management system with access to process, facility, test, diagnostic, design, and any other suitable type of data.

In a further embodiment, at least one of the virtual system(s) is configured to receive the output generated by at least two of the two or more actual systems. For example, multiple wafer scanning inspection tool models/types (e.g., optical and electron beam) may be coupled to a single virtual system such that they can all feed data to the one virtual system. In another embodiment, the virtual system(s) are configured to receive and store the output generated by at least two of the two or more actual systems simultaneously. For example, any of the virtual systems may be configured for simultaneous writing from multiple data sources (e.g., reticle and wafer design). Therefore, the virtual systems may be configured for simultaneous recording from multiple sources to the system.

In one such embodiment, as shown in FIG. 1, both actual system 100 and actual system 102 may be coupled to virtual system 116 so that the virtual system can receive output from both of the actual systems simultaneously or in any other manner. In another such embodiment, as shown in FIG. 2, all of the actual systems shown in this figure and described further above may be coupled to virtual system 216 so that the virtual system can receive output from both of the actual systems simultaneously or in any other manner.

Figure 3:
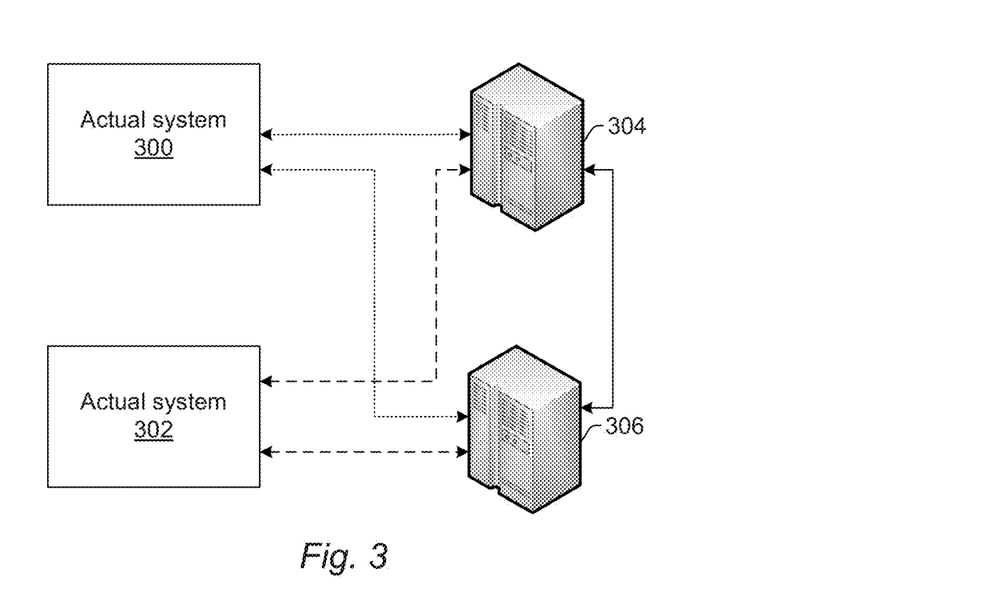

In an additional such embodiment, as shown in FIG. 3, the system may include two or more actual systems, of which only actual system 300 and actual system 302 are shown. These actual systems may include any of the actual systems described further herein. In this embodiment, the system includes two virtual systems 304 and 306. In addition, each of the actual systems may be coupled to each of the virtual systems. For example, as shown in FIG. 3, actual system 300 is coupled to virtual systems 304 and 306 such that output and information can be sent from the actual system to both virtual systems and from both virtual systems to the actual system. In addition, actual system 302 is coupled to virtual systems 304 and 306 in a similar manner.

In one embodiment, the virtual system(s) have the same configuration. In another embodiment, the virtual system(s) have different configurations. For example, when the system includes more than one virtual system, each of the virtual systems may have the same configuration or each of the virtual systems may have different configurations. In addition, when the system includes more than one virtual system, not all of the virtual systems may be coupled to each and every one of the actual systems. Furthermore, the virtual systems may be coupled to each other as shown in FIG. 3 to facilitate transfer of any output, data, information, etc. from one virtual system to another.

Although the virtual systems are shown in the figures as having a particular computer configuration, it is to be understood that the virtual systems may have any suitable computer-like configuration. For example, the virtual system shown in FIG. 1 may be formed of only the processor, memory, and input/output components of the virtual system but not any components that can accept user input (e.g., keyboards, mice, screens, etc.). In this manner, the virtual system may not include all of the components that would normally make up a free-standing fully functional computer system. However, in other instances, the virtual system may resemble a fully functioning computer system in that a user can use the virtual system directly to perform one or more functions using any of the data stored therein. In addition, more than one workstation or user can access the virtual system simultaneously, remotely, and/or wirelessly. For example, as shown in FIG. 1, multiple workstations 118 and 120 can be coupled to the virtual system simultaneously. In this manner, multiple users may access the virtual system or data stored therein and use the virtual system to perform one or more of the functions described further herein.

The embodiments described herein can include any suitable number of actual systems and virtual systems. Therefore, the embodiments described herein can extend the virtual inspector concept by leveraging inspection and review virtualization to its logical extreme. Any or all of the actual and virtual systems included in the system may have standard interfaces and may be managed by an operating system.

The one or more virtual systems are not capable of having the one or more specimens disposed therein. For example, although the virtual systems are configured to perform one or more functions for a specimen, the virtual systems are not configured to perform the one or more functions on the specimen. Instead, the one or more functions for the specimen may be performed on data or other output produced by an actual process performed on the specimen by an actual system. Therefore, unlike the actual systems described herein, the virtual systems may not have any specimen handling capabilities such as stages, motors coupled to stages, specimen handling devices or robots, or the like. In addition, although the virtual systems may be configured to control one or more of the actual systems such that the actual system(s) perform process(es) on an actual specimen, the virtual systems cannot in of themselves perform any actual processes on actual specimens.

The one or more virtual systems are configured to perform one or more functions using at least some of the output received from the two or more actual systems. The one or more functions may be any functions that can normally be performed by any of the actual systems described herein on any of the data, images, or any other output generated by any of the actual systems. For example, the one or more functions may include any functions that can be performed by an electron beam metrology tool on output acquired by one or more detectors of the tool for a wafer or a reticle. Therefore, the virtual systems can be used as a virtual electron beam metrology tool in that it or they can be used as an electron beam metrology tool just without any data acquisition or specimen handling capabilities. In this manner, the virtual systems can provide full replication of the data processing of the actual systems described herein such as electron beam metrology. In addition, those applications can be replicated at run time speeds or faster since the virtual system is not limited by any of the optical or electromechanical constraints associated with data acquisition. Rather, the speed is limited by computation, networking, memory access, etc. (all of which can be tailored by the flexible and expandable characteristics of the embodiments described herein based on the applications that are or will be used to perform).

The systems described herein can also be used as a proxy for a full inspection system (i.e., the inspection system including the imaging elements). For example, the virtual system(s) may be configured to use image data stored therein to perform one or more functions that can be performed by a full inspection system. In addition, the virtual system(s) may be configured to perform such functions offline (without using the full inspection system). Therefore, the virtual system(s) may be used as a substitute for the full inspection system such that functions of the full inspection system can be performed by the virtual system(s) while the full inspection system is free for other functions (e.g., imaging a physical wafer). Functions of a full inspection system that can be performed by the virtual system(s) as a proxy for the kill inspection system include, but are not limited to, defect inspection, defect classification, image defect source analysis, recipe setup, and design based binning.

The system may be configured as a single package containing the hardware and software required to acquire the images and execute all of the algorithms of any of the actual systems described herein. For example, the virtual systems may be configured to function as a BF inspector at kill runtime speed and playback at kill runtime speed. The virtual systems may also be configured to function as an electron beam review tool and/or hot spot inspector-metrology tool at run time speed. In addition, the virtual systems may be configured to replay electron beam detection and classification algorithms at a relatively small fraction of the run time. Such replay can be performed with a transitory configuration allocating the BF processing nodes to electron beam. BF functionality can be embodied in a tool emulator. The input for such functions may include a recipe (including a classifier and a recipe distribution system) and full images generated by a detector of the inspector. The output for such functions may include inspection results in a standard file format such as a KLARF and lot results with attributes and possibly sample flags. Electron beam functionality can also be embodied in a tool emulator. The input for such functions may include a recipe and inspection results such as a sample KLARF or lot results with images generated by inspection, which may include multi-perspective images. The output of such functions may include inspection results in a standard file format such as a KLARF or lot results with multi-perspective images and attributes. The virtual systems may also be configured to perform virtual inspection compatible applications (e.g., new adaptive sampling applications). The inputs to such applications may include recipes, which may include a classifier and data. The outputs may include new or modified recipes including a classifier and old or modified data. Furthermore, a single virtual system could embody multiple wafer scanning inspection tool models and/or types.

The virtual systems described herein may have multiple modes just like actual systems. For example, a virtual system emulating an area inspector may have record, playback, setup, and review modes. In addition, a virtual system emulating an actual review spot inspection tool may have record, playback, setup, and review modes. In addition, actual systems with multiple resource modes may be modeled as separate virtual systems, e.g., electron beam playback with "native" server resources and "super computer" mode. In this state, the playback mode of other virtual systems (e.g., BF) may be unavailable.

In some embodiments, the virtual system(s) are configured to perform at least two of the function(s) simultaneously. For example, the virtual system(s) may perform simultaneous data generation and analysis from one or more physical specimens and/or one or more stored image sources of the specimen(s) and/or one or more modeled or derived virtual representations of the specimen(s). In another embodiment, the virtual system(s) are configured to perform at least two of the function(s) independently of each other. For example, the resources of the virtual systems can be programmatically allocated to "create" virtual tools temporally.

In one embodiment, the virtual system(s) are configured to perform at least one of the function(s) while the two or more actual systems are performing at least one of the one or more processes. The virtual systems may be configured to augment a run time inspection on a metrology or inspection/review tool with resources available on the virtual system(s). In addition, the virtual systems may be configured to generate design-based images in parallel with recording from the physical specimen(s). Furthermore, different types of images (e.g., reticle and wafer images) can be recorded simultaneously by the virtual systems described herein. The actual systems may also perform some processes while the virtual systems are performing other functions, which may or may not be related to the processes being performed by the actual systems. For example, the actual systems may be performing inspection on some wafers while at the same time the virtual system is creating a recipe for a reticle defect review process. In addition, if the actual systems are performing a process, the results of which are to be transferred to the virtual system, and the virtual system is unable to receive the results as the actual process is being performed, the actual system may store the results temporarily until the virtual system is available to receive the results. The control of transfer of information between the virtual and actual systems may reside within the virtual systems.

In an additional embodiment, the output received by the one or more virtual systems includes output generated by one or more detectors of the two or more actual systems. For example, as described above, the virtual systems may be configured to receive output generated by detector(s) of the actual systems via the detectors themselves or via computer subsystems of the actual systems. The output generated by the detectors and received by the virtual systems may include the raw output generated by the detectors or output upon which some function has been performed (e.g., by the computer subsystem of the actual system or some other component of the actual system, e.g., a high pass filter).

In some embodiments, the output received by the one or more virtual systems includes output generated by one or more computer systems of the two or more actual systems. For example, as described above, the virtual systems may be configured to receive output generated by computer subsystems of the actual systems. The output generated by the computer subsystems and received by the virtual systems may include any output that can be generated by the computer subsystems, including output generated based on output of one or more detectors of the actual system. However, the output of the computer subsystems may also include results of some process not performed on output of the one or more detectors. For example, if the computer subsystem of the actual systems performs some function on design data for a wafer or reticle, any information resulting from such functions may also be sent to the virtual systems.

In a further embodiment, the virtual system(s) are configured to store all of the output received from the two or more actual systems indefinitely. In this manner, the system may create persistent data for a specimen (i.e., data that persists in storage media indefinitely until it is deleted intentionally, perhaps by a user). In addition, if the actual systems generated output for an entire specimen, then the output received from the actual systems may include output for the entire specimen. However, if the actual systems generated output for only a portion of an entire specimen, then the output received from the actual systems may include only the output for the portion of the entire specimen. In this manner, both full and partial specimens can be considered. In addition, full reticle and wafer images may be stored on the same virtual system that may be configured as a virtual reticle and wafer inspector. As such, implementations (or modes) span from patch images to full specimen recordings. Furthermore, the stored data can be "surgically" deleted with the intent of keeping what is needed for future use and freeing up storage capacity for future recordings.

In another embodiment, the virtual system(s) are configured to generate information for at least one of the specimen(s) without using the output received from the two or more actual systems and to store the information generated by the virtual system(s) in the virtual system(s). For example, the virtual system(s) may be configured to perform memory intensive applications such as design data indexing and to store the results of such applications. In one such example, the virtual systems may be configured to process design data to determine critical points in the design data and to generate a recipe based on the critical points. In another such example, in one embodiment, the virtual system(s) are configured to acquire results of modeling of one or more fabrication processes that have been or will be performed on at least one of the specimen(s), and the one or more fabrication processes alter one or more characteristics of the at least one specimen. For example, the virtual systems may be configured to perform modeling of the fabrication processes performed on the specimen to simulate what the specimen will "look like" at some point in the process. The virtual systems may also be configured to perform modeling of an actual process performed by one or more of the actual systems to simulate what output of the actual process will "look like" for a specimen on which the actual process is performed. Each of the functions described above may be performed in any suitable manner known in the art.

In some embodiments, the output received from the two or more actual systems includes one or more images of at least one of the specimen(s) acquired using one or more imaging conditions. For example, recording images in multiple optical modes on a given platform is common practice. In this manner, the output received by the virtual system(s) from the actual systems may include an image of a specimen such as a wafer or a reticle acquired in any manner (e.g., optical or electron beam inspection, review, or metrology) at one or more stages of the implementation process in one or more of the available imaging conditions.

In another embodiment, the output received from the two or more actual systems includes at least first and second images of at least one of the specimen(s) acquired after different fabrication processes have been performed on the at least one specimen, and the different fabrication processes alter one or more characteristics of the at least one specimen. In this manner, the virtual system may store different images of the same specimen acquired at different points in a fabrication process performed on the specimen. In one such example, the virtual system may receive and store an image of a wafer after a lithography process and an image of the wafer after an etch process. In another example, the virtual system may receive and store an image of a wafer after a chemical-mechanical polishing process and an image of the wafer after a deposition process. Storing different output for the same specimen at different points in its fabrication process is advantageous for performing additional functions described herein (e.g., defect source analysis).

The virtual system(s) may be configured to acquire and store information from sources other than the actual systems as well as the actual systems. For example, the virtual system(s) may be configured to acquire and store a physical design for devices being formed on or with the specimen(s) and any optical or simulated derivation of data from one or more actual systems or the physical design data. In one such example, the virtual system(s) may acquire the design data from an electronic design automation (EDA) tool that generated the design data or from another storage medium in which the design data is stored. The virtual system(s) may also acquire layout intent data (e.g., from the EDA tool, a storage medium, etc.). Therefore, the virtual system(s) may acquire "pre-wafer" data (i.e., data that existed before the creation of a wafer with that data). Such "pre-wafer" data may also include reticle information from one or more of the actual systems described herein. In addition, simulated data may be acquired from the system that generated the simulated data or a storage medium in which the simulated data is stored. The virtual system(s) may also be configured to simulate such data as described further herein. In addition, the simulated data may include multiple sets of simulated data, each set generated for one of the physical planes or layers of a specimen such as a wafer. Therefore, each set of simulated data may correspond to one of different "data planes" for a specimen, and each of the "data planes" can be calculated from design data using equipment and/or process modeling.

In some embodiments, the virtual system(s) are configured to acquire a modeled representation of an intended physical state of at least one of the specimen(s). For example, the virtual system(s) may be configured to acquire and store modeled. representation of an intended physical implementation of the specimen. In other words, the virtual system(s) may be configured to acquire simulated images at the wafer plane. The virtual system(s) may be configured to generate the modeled representation by using context from any stage of the design process and modeling of the physical implementation process.

The virtual system(s) may also be configured to acquire a modeled representation of an image that would be generated by one of the actual systems described herein or an image that is modeled based on an image or other output of one or more of the actual systems. In this manner, the virtual system(s) may be configured to acquire simulated images at the equipment imaging plane. The virtual system(s) may acquire the modeled representation by generating the modeled representation. Alternatively, an actual system may generate the modeled representation, and the virtual system(s) may acquire the modeled representation from the actual system. In a similar manner, the virtual systems may acquire an image modeled based on other output of the actual system(s) by performing the modeling or by receiving such a modeled image from the actual system that generated it. In some such examples, the virtual system(s) may be configured to acquire reticle images including database images modeled from design including modeled derivatives of acquired images (Teron aerial, resist, wafer plane, etc.) and aerial image optics. In addition, the virtual systems may acquire database images modeled from design for electron beam wafer inspection and/or review.

In an additional embodiment, the virtual system(s) are configured to acquire context-based information for a device being formed with at least one of the specimen(s). For example, as described above, the virtual systems may be configured to acquire layout intent data, which is also commonly referred to as designer intent data (i.e., how the designer intended the design to be fabricated on a wafer). The context-based information may be acquired from an EDA or other suitable tool. In addition, the context-based information may be generated by the virtual system. For example, the virtual system may receive design data and then determine context-based information for the design data. The context-based information may be used by the virtual systems to create recipes for context-based processes such as context-based inspection (CBI) or for any other purposes.

As will be apparent from the description provided herein, the virtual system(s) may be configured to store a wide variety and a substantial amount of information. Therefore, the virtual systems preferably have configurations and capabilities to store and access all of the data, which may include randomly accessing mass images distributed across a disk farm. In addition, for virtual specimens and associated state tracking, derived data layers need to be managed efficiently. The systems described herein may be configured for data management that may include storage, access, analysis, and validation. For storage, the data that is stored may include a mixture of conventional defect data and massive stored images. In addition, the systems may be configured to have standard database administration capability such as backup and restore. For data access, the system may be configured to treat the massive stored images as SQL addressable databases. For data analysis, the system preferably has compatibility with the algorithm(s) used to collect the data. In addition, the data set(s) must be compatible with the analysis recipes.

In some embodiments, at least one of the virtual system(s) is configured to control operation of at least one of the two or more actual systems. For example, any of the virtual systems may be configured to control the operation of any of the actual systems and virtual systems connected to it. In addition, any of the virtual systems may be configured to enable manual or automated modification of the operation of any of the actual and virtual systems connected thereto. Controlling the operation of the actual system(s) may also include scheduling when the actual system(s) are used to perform certain processes. For example, the virtual systems may be configured for look-ahead factory resource scheduling and a programmable state machine-based resource allocation/management scheme may be included. In this manner, the system may be configured for state machine resource management with took-ahead features linked to a factory automation system. In addition, the virtual systems may be configured for internal job queue management across the actual and virtual systems included in the system with consideration of factory level job scheduling (e.g., management availability for forthcoming record jobs). Such management may take into consideration the states of the actual and virtual systems such as what actual and virtual systems currently exist and the state of each system. In addition, such management may take into consideration schedules such as what systems are scheduled to exist and the schedule for each system. In addition, the virtual system(s) may be configured for monitoring the tool state and health history of one or more of the actual systems. If the tool state and/or health history of an actual system changes, a virtual system may take control of the actual system to diagnose and correct any problems with the actual system. The virtual systems may also manage state and data collisions, which may include "priority interrupts" and "error detection" recovery. Furthermore, the systems described herein may be configured for machine control that may include managing "multiple machines in one" state machine and transitions. The switching process performed by the virtual systems may be controlled by a state machine that also interacts with external factory automation. The virtual systems may be configured to use internal state polling and state change commands using standard factory automation protocols to enable smooth development of externally available factory automation capabilities. The virtual systems may also use a Broker Architectural Pattern to structure distributed software systems with decoupled components that interact by remote server invocations. A broker component may be responsible for coordinating communication such as forwarding requests as welt as for transmitting results and exceptions.

In an embodiment, the virtual system(s) are configured to control operation of at least one of the two or more actual systems and at least one of the one or more virtual systems independently. For example, any of the virtual systems may be configured to independently control the operation of any of the actual systems and virtual systems connected to it. Such control may be manual or automated. In addition, the virtual systems may be configured for direct control of any of the actual systems described herein.

In an additional embodiment, the virtual system(s) are configured to synchronize operation of at least one of the two or more actual systems and at least one of the virtual system (s) in real time. For example, any of the virtual systems may be configured to synchronize the operation of any of the actual systems and virtual systems connected to it in real time. Such synchronization may be manual or automated. In addition, any of the virtual systems may be configured to adjust recipe parameters to synchronize the actual systems in any mode. The use of standard factory automation protocol can be extended to the virtual systems.

In some embodiments, the virtual system(s) are configured to acquire at least one recipe for at least one of the one or more processes performed by the two or more actual systems. For example, the virtual systems may be configured to import a recipe from a storage device. In addition, in another embodiment, the virtual system(s) are configured to acquire from the two or more actual systems one or more recipes that were used to generate the output received from the two or more actual systems. For example, when an actual system sends output to the virtual system, the actual system may send the recipe that was used to generate the output. In this manner, the virtual system may acquire recipes from actual systems corresponding to the output being sent from the actual systems. If the recipes are not sent automatically with their corresponding output, the virtual systems may request such recipes from the virtual systems. Receiving the recipes corresponding to the output may be important for determining the conditions under which the output (e.g., images) were acquired.

In another embodiment, the virtual system(s) are configured to generate at least one recipe for at least one of the one or more processes performed by the two or more actual systems. In this manner, the embodiments described herein can perform recipe setup or recipe creation. The embodiments described herein provide efficient offline setup of the actual systems described herein, which can be performed using any of the data that is stored in the virtual system(s) or can be acquired or generated by the virtual system(s). For example, recipe setup may be performed using design data, output generated by an optical wafer inspection system, and a SEM. In addition, recipe setup may include automated adaptive sampling. The virtual system(s) may also co-optimize multiple inspection recipes on multiple platforms. The virtual system(s) may also create more complex electron beam inspection and/or review recipes. In addition, the virtual system(s) provide a deployable, user-accessible, and field adaptive ecosystem for complex recipe co-optimization. Furthermore, the virtual system(s) can be configured for recipe compilation, generation, and subsequent distribution.

A recipe created by the virtual systems may include data or output acquisition conditions that include physical interaction with a specimen as well as defect detection or metrology algorithm settings and post-processing analysis. The data acquisition conditions may be for acquiring data from any sensor type of the actual system including imaging sensors. The post-processing analysis can include such operations as sampling for subsequent operations, filtering, data or image "fusion," systematic pattern failure, and any other post-processing analysis that can be performed by the actual systems described herein.

The virtual systems described herein may also enable machine learning from a single session or from session to session. For example, in a further embodiment, the virtual system(s) are configured to alter at least one recipe for at least one of the one or more processes performed by the two or more actual systems based on the output received from at least one of the two or more actual systems. In one such embodiment, one or more recipe conditions can be programmatically updated based on learning from prior data acquisition and analysis. Recipe changes can be triggered manually, semi-automatically, or automatically. The prior data can be from any of the sources connected to the virtual systems. The prior data can also be generated in quasi-real time (e.g., as the data is being acquired, the recipe can be altered based on the data). The prior data can also be from a persistent historical data source for one or more of the connected physical and virtual tools. The recipe conditions that are altered may include substantially high precision care areas for discovered patterns and/or regions of interest.

The virtual systems may also be configured to alter a recipe for one of the actual systems based on results generated by another of the actual systems. For example, the virtual systems may be configured for driving both automated and interactive metrology and inspection. In one such example, the virtual systems may be configured to alter a defect review recipe (e.g., an electron beam review recipe) based on results from an inspection system. In a similar manner, the virtual systems may be configured to alter an inspection recipe (e.g., a light-based or electron beam-based inspection recipe) based on results from a defect review system. As such, the virtual systems may be configured to alter recipes for the actual systems using feedforward and feedback control schemes. In addition, the virtual system(s) may be configured for autonomous recipe optimization with feedforward and/or feedback data acquisition across any of the available data sources. As further described herein, the virtual systems may be configured to alter recipes for the actual systems in pseudo real time. Therefore, the virtual systems may also be configured for pseudo in-situ control of the actual systems.

The virtual systems described herein may also be configured to use metrology and electrical test data in new ways. For example, the virtual systems are useful for implementing hybrid metrology and inspection applications in which the substantially high area coverage of an inspection system is convolved with the substantially high precision and accuracy of a metrology tool (for, e.g., critical dimension, overlay, morphology, etc.). For such applications, tightly coupled metrology tools may be combined with any of the inspection systems described herein. The interactive or automated (with or without a formal recipe) remote control of metrology systems is a direct benefit of the rapid learning and discovery loops enabled by the systems described herein. For example, the systems may be used for driving a reticle inspection or metrology tool to locations where wafer inspection and/or review indicate that there are suspected explanations for wafer-level observations. In another example, the virtual systems may be configured for integration of design and image data with attribute generation to assist detection or classification.

The virtual systems may also be configured for interactive or automated control of image acquisition (generation) sources such as the actual systems from the virtual system(s) or a recipe generated on the virtual system(s). The motivation for such control can be to benefit from previous learning that has occurred on the virtual systems. The parameters of the recipes that are altered by the virtual systems may also include the sampling used in the recipes. For example, the virtual systems may be configured for adaptive sampling of points or regions of interest on the specimen in a particular imaging or modeling mode. In addition, the virtual systems may be configured for adaptive sampling along with automatic defect classification (ADC) to create a self-learning optical-electron beam classification engine for high defect volumes, which can be used for engineering experiments or ultimately in production under factory automation. Such electron beam adaptive sampling can be performed at runtime in an automatic mode. In addition, the ADC results can drive adaptation of the review sample weightings.

The virtual systems described herein may also be configured to generate a recipe for itself or for another virtual system. For example, the virtual system(s) may store the recipe that was used to generate a stored result. In other words, the virtual system(s) may store the recipes that are used to perform the one or more functions of the virtual systems and the recipe(s) can be associated with any results of one or more such functions that were performed using the recipe(s). Unlike recipe creation or modification for the actual systems, recipe creation or modification for the virtual systems does not necessarily include data acquisition using a physical specimen. For example, for virtual systems, recipe modifications may be limited to defect detection or metrology algorithm settings and post-processing analysis that is performed using stored data. In addition, the recipe modifications may be similar to those for actual systems but the recipe modifications may be limited to defect detection or metrology algorithm settings and post-processing analysis that is performed using stored data.

In an additional embodiment, the virtual system(s) are configured to alter at least one recipe for at least one of the one or more processes performed by the two or more actual systems as the at least one process is being performed on at least one of the one or more specimens and based on output generated during the at least one process. In other words, recipe parameter values can be changed on the fly. For example, a virtual system can process data streaming from one or more virtual or actual systems and update a recipe parameter. Recipe parameters that can be changed on the fly thereby improving the net result of the inter-related processes include, but are not limited to, parameters of sampling such as sample tree weightings, care areas, or algorithm parameters such as thresholds.

In one embodiment, the virtual system(s) are configured to create care areas for at least one recipe for at least one of the one or more processes performed by the two or more actual systems based on the output received from the two or more actual systems or information generated by the one or more virtual systems. The care areas can be generated in any suitable manner. In some embodiments, the care areas can be generated for one process performed by an actual or virtual system based on output generated by another actual system. In other words, care areas for one process can be generated based on results of another process. In addition, care areas can be generated from sources other than actual process results. For example, the virtual systems may be configured to generate care areas based on design data. In addition, the virtual systems may be configured to alter or update care areas for any process performed by an actual system or any function performed by a virtual system based on any of the information that is available to the virtual systems.

The recipes used and created by the embodiments described herein can be substantially different from all other previously used yield control related recipes. For example, as far as the recipe hierarchy is concerned, a conventional single layer inspection recipe concept is obsolete for the embodiments described herein. Instead, a conventional recipe may become a component of a "super recipe". A super recipe may have a single platform and is preferably self-consistent across layers. A generalized super recipe may be a multi-platform recipe and may preferably be self-consistent across technical domains. In the context of the embodiments described herein, the term "self-consistent" simply means that various recipes collect data or generate output in such a manner that the data or output can be used together (e.g., via common wafer coordinates) and such that any data required by any one recipe is available to the virtual system.

Recipe types may include data acquisition recipes, data processing recipes, and data analysis recipes. For data acquisition recipes, all data collection is preferably compatible with any pre-existing data. In addition, all data collection is preferably forward compatible with required future data. For data processing recipes, the recipes may be for image processing, image fusion, image subtraction (within specimen, specimen-to-specimen, etc.), multi-source data fusion (e.g., image+design). The output of a data processing step may be a new "virtual specimen" which in turn can be the input to another data processing or data analysis step. Furthermore, "virtual specimen" state tracking and process sequencing are important to keep data valid. For data analysis recipes, the recipes may include inspection, defect source analysis, prior level nuisance suppression, attribute extraction, measurements, and the like. The complexity of the algorithms and data dictates that analysis be tightly controlled and embodied in a "correct by construction" recipe that is compatible with the scenario.

For experiment execution, dependencies on prior data being qualified include self-consistency of the recipe states, algorithm states, tool states, and specimen states through the life of the experiment for generalized inspection). For recipe management, standard concepts in recipe management should be applied to the "super recipes" such as access, verification, distribution, security, and change control.

As can be seen from the above description, therefore, recipe setup and design of experiment work traditionally done manually and serially with actual tools can be performed concurrently and/or adaptively by the systems described herein across a broader variable space than previously possible or practical by fully leveraging, in a machine learning framework: acquired and generated image planes; automated defect classification and metrology; inspection and metrology virtualization; factory automation and cell controller principles; data dependent work flows and adaptive recipes; and high speed networking and adaptive resource allocation.

In some embodiments, the output received from the two or more actual systems includes at least first and second output for at least one of the one or more specimens generated after at least first and second fabrication processes have been performed on the at least one specimen, respectively, the first and second fabrication processes alter one or more characteristics of the at least one specimen, and the virtual system(s) are configured to perform the one or more functions using both the first and second output. In other words, the virtual systems may use images (or other output) generated for a specimen at different points in its fabrication process to perform one or more functions for the specimen. For example, the virtual system(s) may be configured for multi-layer determination of defect sources by using random access to previously acquired (or calculated) images to make a determination as to the preexistence of a defect at a previous layer. In one such example, the virtual system may be configured to use an image of a specimen generated after lithography to evaluate defects detected in an image of the specimen generated after etch. A related operation is using the previous layer image data for noise filtering.

In another embodiment, the virtual system(s) are configured to acquire information for an electrically identified hot spot on a wafer, the output received from the two or more actual systems include output, for the wafer and a reticle used to perform at least one process on the wafer, generated by the two or more actual systems prior to electrical testing of the wafer that electrically identified the hot spot, and the one or more virtual systems are configured to diagnose the hot spot based on the output generated prior to the electrical testing. A "hot spot" may be generally defined as a location in the design data printed on the wafer at which a killer defect may be present. When a wafer hot spot is identified electrically, diagnosis and monitoring recipe setup can be performed on the virtual systems containing any combination of reticle, optical wafer, and electron beam wafer images. Multiple layers can be considered simultaneously. In addition, the physical wafer or reticle can be interrogated on any appropriate metrology or inspection system using feedforward or feedback control. In a similar manner, defect source analysis may be performed using images generated by any of the actual and virtual systems described herein.

In some embodiments, the output received from the two or more actual systems includes at least first and second output for at least one of the one or more specimens generated after at least first and second fabrication processes have been performed on the at least one specimen, respectively, the first and second fabrication processes alter one or more characteristics of the at least one specimen, and the virtual system(s) are configured to determine one or more parameters of at least one of the one or more processes to be performed on the at least one specimen by at least one of the two or more actual systems based on the first and second output. In other words, the virtual systems may use images (or other output) generated for a specimen at different points in its fabrication process to create, alter, or update an actual process recipe. In one such example, the virtual systems may use images generated for a wafer after lithography and after etch to create a recipe for a metrology or inspection process for the wafer, which may be performed after the etch process and before any other fabrication process is performed on the wafer or after another fabrication step has been performed on the wafer.

In a further embodiment, the virtual system(s) are configured to generate a standard reference die using any combination of the output received from the two or more actual systems and any other information stored in or acquired by the one or more virtual systems. In this manner, the virtual system(s) may generate a standard reference from any sources stored on or connected to the virtual systems. The standard reference may be generated in any suitable manner and may be used in an inspection process in which inspection output is compared to the standard reference to detect defects.

In another embodiment, the virtual system(s) are configured to generate an image of the specimen using image data stored in the virtual system(s) and at least one additional source of data for the wafer. In this manner, the virtual system(s) may be configured to perform image fusion. In multi-layer image fusion, images may be formed by combining images acquired at different steps in the process flow computationally. In multi-mode image fusion, images may be formed by combining images acquired using different optical modes at a given process step. The image fusion may also be cross-platform image fusion that combines images from any combination of inspector types and related specimen types. For example, the inspector types may include electron beam, optical, patterned, unpatterned, review tools, and any other inspector types described herein. In addition, the image fusion may be performed using any image data generated by any of the actual or virtual systems described herein. The images that are combined may include images computed for one or more layers on the wafer via modeling and/or combined with any of the above-described sources.

Image fusion may not include simply overlaying multiple sources of data (although such overlay may also be performed by the systems described herein). Instead, image fusion may include combining multiple sources of data to generate a composite image. Image fusion may also be performed as described in commonly owned U.S. Pat. No. 8,223,327 issued on Jul. 17, 2012 to Chen et al., which is incorporated by reference as if fully set forth herein. The virtual system(s) may be configured to detect defects using the images generated by image fusion.

The system embodiments described herein may be configured to export results of any of the one or more functions performed by the virtual system(s) in any suitable manner. For example, the system preferably has support infrastructure that is compatible with standard factory recipes and data automation. In this manner, the virtual system(s) may export results generated by the virtual system(s) to a manufacturing execution system or other software infrastructure in a wafer fab and/or an automated process control (APC) system. The APC system can use the information exported by the virtual system(s) for feedback and/or feedforward between the virtual system(s) and any one or more fabrication tools in the fab.

As can be seen by the description of the embodiments provided herein, the systems configured as described herein are different from currently used inspection and other yield control-related systems. For example, "correct by construction" design methods, "process integration" thinking, and extraordinary systems engineering discipline should be applied to all aspects of the embodiments described herein. In particular, an unprecedented number of logistical constraints need to be satisfied. In addition, the complexity exceeds what is achievable with conventional inspection and measurement approaches. Furthermore, the state of actual tools that generate data that is consumed by the virtual systems must now consider stacked alignment tolerances rather than meeting the requirements for a single inspection. This is analogous to process integration considerations for semiconductor manufacturing.

In addition, the key factors to be considered in the systems described herein are source tool monitoring, machine control, and algorithms. As far as source tool monitoring is concerned, tools states can be more observable to meet tighter data compatibility constraints. In addition, the embodiments described herein drive the need for "big data" analysis. As far as machine control is concerned, the scope of the system may be determined based on if a requested machine is achievable with the current system instantiation. In addition, the state of the system may be determined based on if a requested machine is currently available. Furthermore, a state change for the system can be determined based on if the system can safely transition to the requested state. The algorithms that are used by and/or created by the systems described herein may also take into consideration multi-mode dependencies, multi-tool dependencies (e.g., constraints on which tools are used for prior data, constraints on tool states, etc.), and multi-layer dependencies (e.g., required pre-existing data must exist and be accessible, pre-existing and new data must be mutually compatible with the algorithm, etc.).

Each of the embodiments of the system described above may be further configured according to any other embodiment(s) described herein. The embodiments described herein may also be further configured to perform any of the functions described in U.S. Pat. No. 7,522,664 issued on Apr. 21, 2009 to Bhaskar et al., U.S. Pat. No. 7,570,796 issued on Aug. 4, 2009 to Zafar et al., U.S. Pat. No. 7,676,077 issued on Mar. 9, 2010 to Kulkarni et al., U.S. Pat. No. 7,877,722 issued on Jan. 25, 2011 to Duffy et al., U.S. Pat. No. 8,041,103 issued on Oct. 18, 2011 to Kulkarni et al., U.S. Pat. No. 8,126,255 issued on Feb. 28, 2012 to Bhaskar et al., U.S. Pat. No. 8,139,843 issued on Mar. 20, 2012 to Zafar et al., U.S. Pat. No. 8,194,968 issued on Jun. 5, 2012 to Park et al, and U.S. Pat. No. 8,611,639 issued on Dec. 17, 2013 to Kulkarni et al., which are incorporated by reference as if fully set forth herein. The embodiments described herein may be further configured as described in these patents.

Another embodiment relates to a method for performing one or more actual processes and one or more virtual processes for a specimen. The method includes performing one or more processes on one or more specimens with two or more actual systems while the one or more specimens are disposed within the two or more actual systems, which may be performed as described further herein. The one or more specimens include a wafer and/or any other specimens described herein. The method also includes receiving output generated by the two or more actual systems with one or more virtual systems coupled to the two or more actual systems, which may be performed as described further herein. In addition, the method includes sending information from the one or more virtual systems to at least one of the two or more actual systems, which may be performed as described further herein. The method further includes performing one or more functions with the one or more virtual systems using at least some of the output received from the two or more actual systems, which may be performed as described further herein. The one or more virtual systems are not capable of having the one or more specimens disposed therein.

The embodiment of the method described above may be performed by any of the system embodiments described herein. In addition, the embodiment of the method described above may include performing any step(s) and/or function(s) of any other embodiment(s) described herein.

Figure 4:
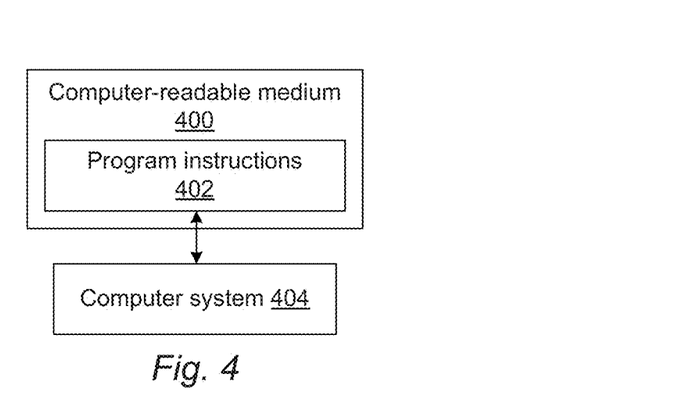
FIG. 4 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for performing one or more actual processes and one or more virtual processes for a specimen. One such embodiment is shown in FIG. 4. In particular, as shown in FIG. 4, non-transitory computer-readable medium 400 includes program instructions 402 executable on computer system 404.

The computer-implemented method includes receiving output generated by two or more actual systems with one or more virtual systems coupled to the two or more actual systems, which may be performed as described further herein. The two or more actual systems perform one or more processes on one or more specimens while the one or more specimens are disposed within the two or more actual systems, and the one or more specimens include a wafer and/or any other specimens described herein. The computer-implemented method also includes sending information from the one or more virtual systems to at least one of the two or more actual systems, which may be performed as described further herein. In addition, the computer-implemented method includes performing one or more functions with the one or more virtual systems using at least some of the output received from the two or more actual systems, which may be performed as described further herein. The one or more virtual systems are not capable of having the one or more specimens disposed therein. The computer-implemented method for which the program instructions are executable may include any other step(s) described herein.

Program instructions 402 implementing methods such as those described herein may be stored on computer-readable medium 400. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Further modifications and alternative embodiments of various aspects of the invention will be apparent to those skilled in the art in view of this description. For example, generalized virtual inspectors are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to perform one or more actual processes and one or more virtual processes for a specimen, comprising:

two or more actual systems configured to perform one or more processes on one or more specimens while the one or more specimens are disposed within the two or more actual systems, wherein the one or more specimens comprise a wafer, wherein the two or more actual systems comprise a first actual system having a first configuration and a second actual system having a second configuration, and wherein the first second configurations are different from each other; and one or more other systems coupled to the two or more actual systems to thereby receive output generated by the two or more actual systems and to send information to the two or more actual systems, wherein the one or more other systems are configured to perform one or more functions using at least some of the output received from the two or more actual systems, wherein the one or more other systems are further configured to replicate data processing of the first actual system having the first configuration and to replicate data processing of the second actual system having the second configuration different from the first configuration, and wherein the one or more other systems are not capable of having the one or more specimens disposed therein.

2. The system of claim 1, wherein the one or more specimens further comprise a reticle.

3. The system of claim 1, wherein the wafer has incompletely fabricated devices formed thereon.

4. The system of claim 1, wherein the wafer has completely fabricated devices formed thereon.

5. The system of claim 1, wherein the two or more actual systems further comprise two of the same systems.

6. The system of claim 1, wherein the two or more actual systems are further configured to perform the one or more processes on more than one of the one or more specimens simultaneously.

7. The system of claim 1, wherein the two or more actual systems are further configured to perform the one or more processes on the one or more specimens independently of each other.

8. The system of claim 1, wherein the two or more actual systems further comprise at least one reticle inspection system or reticle defect review system.

9. The system of claim 1, wherein the two or more actual systems further comprise at least one wafer inspection system or wafer defect review system, and wherein the at least one wafer inspection system or wafer defect review system is a light-based system.

10. The system of claim 1, wherein the two or more actual systems further comprise at least one wafer inspection system or wafer defect review system, and wherein the at least one wafer inspection system or wafer defect review system is an electron beam-based system.

11. The system of claim 1, wherein the two or more actual systems further comprise at least one metrology system.

12. The system of claim 1, wherein the two or more actual systems further comprise at least one wafer testing system, and wherein the wafer testing system comprises an electrical testing-based system.

13. The system of claim 1, wherein the one or more other systems have the same configuration.

14. The system of claim 1, wherein the one or more other systems have different configurations.

15. The system of claim 1, wherein the one or more other systems are further configured to perform the one or more functions simultaneously.

16. The system of claim 1, wherein the one or more other systems are further configured to perform the one or more functions independently of each other.

17. The system of claim 1, wherein the one or more other systems are further configured to perform at least one of the one or more functions while the two or more actual systems are performing at least one of the one or more processes.

18. The system of claim 1, wherein the output received by the one or more other systems comprises output generated by one or more detectors of the two or more actual systems.

19. The system of claim 1, wherein the output received by the one or more other systems comprises output generated by one or more computer systems of the two or more actual systems.

20. The system of claim 1, wherein the one or more other systems are further configured to store all of the output received from the two or more actual systems indefinitely.

21. The system of claim 1, wherein the one or more other systems are further configured to generate information for at least one of the one or more specimens without using the output received from the two or more actual systems and to store the information generated by the one or more other systems in the one or more other systems.

22. The system of claim 1, wherein the output received from the two or more actual systems comprises one or more images of at least one of the one or more specimens acquired using one or more imaging conditions.

23. The system of claim 1, wherein the output received from the two or more actual systems comprises at least first and second images of at least one of the one or more specimens acquired after different fabrication processes have been performed on the at least one specimen, and wherein the different fabrication processes alter one or more characteristics of the at least one specimen.

24. The system of claim 1, wherein the one or more other systems are further configured to acquire a modeled representation of an intended physical state of at least one of the one or more specimens.

25. The system of claim 1, wherein the one or more other systems are further configured to acquire context-based information for a device being formed with at least one of the one or more specimens.

26. The system of claim 1, wherein the one or more other systems are further configured to acquire results of modeling of one or more fabrication processes that have been or will be performed on at least one of the one or more specimens, and wherein the one or more fabrication processes alter one or more characteristics of the at least one specimen.

27. The system of claim 1, wherein at least one of the one or more other systems is further configured to control operation of at least one of the two or more actual systems.

28. The system of claim 1, wherein the one or more other systems are further configured to control operation of at least one of the two or more actual systems and at least one of the one or more other systems independently.

29. The system of claim 1, wherein the one or more other systems are further configured to synchronize operation of at least one of the two or more actual systems and at least one of the one or more other systems in real time.

30. The system of claim 1, wherein the one or more other systems are further configured to acquire at least one recipe for at least one of the one or more processes performed by the two or more actual systems.

31. The system of claim 1, wherein the one or more other systems are further configured to generate at least one recipe for at least one of the one or more processes performed by the two or more actual systems.

32. The system of claim 1, wherein the one or more other systems are further configured to alter at least one recipe for at least one of the one or more processes performed by the two or more actual systems based on the output received from at least one of the two or more actual systems.

33. The system of claim 1, wherein the one or more other systems are further configured to alter at least one recipe for at least one of the one or more processes performed by the two or more actual systems as the at least one process is being performed on at least one of the one or more specimens and based on output generated during the at least one process.

34. The system of claim 1, wherein the one or more other systems are further configured to create care areas for at least one recipe for at least one of the one or more processes performed by the two or more actual systems based on the output received from the two or more actual systems or information generated by the one or more other systems.

35. The system of claim 1, wherein the one or more other systems are further configured to acquire from the two or more actual systems one or more recipes that were used to generate the output received from the two or more actual systems.

36. The system of claim 1, wherein at least one of the one or more other systems is further configured to receive the output generated by at least two of the two or more actual systems.

37. The system of claim 1, wherein the output received from the two or more actual systems comprises at least first and second output for at least one of the one or more specimens generated after at least first and second fabrication processes have been performed on the at least one specimen, respectively, wherein the first and second fabrication processes alter one or more characteristics of the at least one specimen, and wherein the one or more other systems are further configured to perform the one or more functions using both the first and second output.

38. The system of claim 1, wherein the one or more other systems are further configured to acquire information for an electrically identified hot spot on a wafer, wherein the output received from the two or more actual systems comprises output, for the wafer and a reticle used to perform at least one process on the water, generated by the two or more actual systems prior to electrical testing of the wafer that electrically identified the hot spot, and wherein the one or more other systems are further configured to diagnose the hot spot based on the output generated prior to the electrical testing.

39. The system of claim 1, wherein the output received from the two or more actual systems comprises at least first and second output for at least one of the one or more specimens generated after at least first and second fabrication processes have been performed on the at least one specimen, respectively, wherein the first and second fabrication processes alter one or more characteristics of the at least one specimen, and wherein the one or more other systems are further configured to determine one or more parameters of at least one of the one or more processes to be performed on the at least one specimen by at least one of the two or more actual systems based on the first and second output.

40. The system of claim 1, wherein the one or more other systems are further configured to receive and store the output generated by at least two of the two or more actual systems simultaneously.

41. The system of claim 1, wherein the one or more other systems are further configured to generate a standard reference die using any combination of the output received from the two or more actual systems and any other information stored in or acquired by the one or more other systems.

42. A method for performing one or more actual processes and one or more virtual processes for a specimen, comprising:
   performing one or more processes on one or more specimens with two or more actual systems while the one or more specimens are disposed within the two or more actual systems, wherein the one or more specimens comprise a wafer, wherein the two or more actual systems comprise a first actual system having a first configuration and a second actual system having a second configuration, wherein the first and second configurations are different from each other, wherein the two or more actual systems further comprise at least a specimen handling device configured to control a position of the one or more specimens within the two or more actual systems, a detector configured to generate output for the one or more specimens, and one or more computer subsystems configured to perform some function on the output generated by the detector;
   receiving output generated by the two or more actual systems with one or more other systems coupled to the two or more actual systems, wherein the one or more other systems comprise at least a computer processor, memory, and input/output components;
   sending information from the one or more other systems to at least one of the two or more actual systems;
   performing one or more functions with the one or more other systems using at least some of the output received from the two or more actual systems;
   replicating data processing of the first actual system having the first configuration with the one or more other systems; and
   replicating data processing of the second actual system having the second configuration different from the first configuration with the one or more other system, wherein the one or more other systems are not capable of having the one or more specimens disposed therein.

43. A non-transitory computer-readable medium, storing program instructions executable on a computer system for performing a computer-implemented method for performing one or more actual processes and one or more virtual processes for a specimen, wherein the computer-implemented method comprises:
   receiving output generated by two or more actual systems with one or more other systems coupled to the two or more actual systems, wherein the two or more actual systems perform one or more processes on one or more specimens while the one or more specimens are disposed within the two or more actual systems, wherein the one or more specimens comprise a wafer, wherein the two or more actual systems comprise a first actual system having a first configuration and a second actual system having a second configuration, wherein the first and second configurations are different from each other, wherein the two or more actual systems further comprise at least a specimen handling device configured to control a position of the one or more specimens within the two or more actual systems, a detector configured to generate output for the one or more specimens, and one or more computer subsystems configured to perform some function on the output generated by the detector, and wherein the one or more other systems comprise at least a computer processor, memory, and input/output components;
   sending information from the one or more other systems in at least one of the two or more actual systems;
   performing one or more functions with the one or more other systems using at least some of the output received from the two or more actual systems;
   replicating data processing of the first actual system having the first configuration with the one or more other systems; and
   replicating data processing of the second actual system having the second configuration different from the first configuration with the one or more other systems, wherein the one or more other systems are not capable of having the one or more specimens disposed therein.

* * * * *